United States Patent [19]

Hammerich et al.

[11] Patent Number: 5,339,674
[45] Date of Patent: Aug. 23, 1994

[54] METHOD AND APPARATUS FOR THE TRANSMISION OF AN ACOUSTIC SIGNAL IN A PHOTOACOUSTIC CELL

[75] Inventors: Mads Hammerich, Hilleroed; Jes O. Henningsen, Stenloese, both of Denmark; Ari Olafsson, Reykjavik, Iceland

[73] Assignee: FLS Airlog A/S, Denmark

[21] Appl. No.: 927,655

[22] PCT Filed: Mar. 4, 1991

[86] PCT No.: PCT/DK91/00061

§ 371 Date: Sep. 1, 1992

§ 102(e) Date: Sep. 1, 1992

[87] PCT Pub. No.: WO91/14176

PCT Pub. Date: Sep. 19, 1991

[30] Foreign Application Priority Data

May 3, 1990 [DK] Denmark ............................ 562/90

[51] Int. Cl.[5] .......................................... G01N 21/00
[52] U.S. Cl. .................................. 73/24.02; 356/432
[58] Field of Search ............... 73/24.01, 24.02, 24.03; 356/432, 433

[56] References Cited

U.S. PATENT DOCUMENTS

| | | | |
|---|---|---|---|
| 2,963,899 | 12/1960 | Martin et al. | 73/24.01 |
| 3,659,452 | 5/1972 | Atwood et al. | 73/31.04 |
| 3,893,771 | 7/1975 | Bell | 356/402 |
| 3,938,365 | 2/1976 | Dewey, Jr. | 73/24.02 |
| 4,253,770 | 3/1981 | Horba | 356/433 |
| 4,277,179 | 7/1981 | Bruce | 356/433 |
| 4,372,149 | 2/1983 | Zharov | 73/24.02 |
| 4,740,086 | 4/1988 | Oehler et al. | 356/432 |
| 4,817,413 | 4/1989 | Asano et al. | 73/24.02 |

FOREIGN PATENT DOCUMENTS

344234 3/1960 Switzerland .
2148487 10/1983 United Kingdom .

OTHER PUBLICATIONS

"A Toxic Gas Monitor with ppb Sensitivity Using An Automated Laser Optoacoustic Spectrometer", *Laser + Electro-Optik*, vol. 11 (1979).

Primary Examiner—Jill A. Johnston
Assistant Examiner—Laura E. Collins
Attorney, Agent, or Firm—Brumbaugh, Graves, Donohue & Raymond

[57] ABSTRACT

The microphone in a photoacoustic cell that is part of an apparatus for photoacoustic analysis of at least one substance is protected against the harmful effects from the analyzed substance by sonically communicating the microphone with the excitation zone through a waveguide that is at least partly located within the excitation zone. The substance to be analyzed is supplied to the excitation zone, in which zone an acoustic signal is generated by an acoustic frequency modulation of an optical signal directed into the substance in the excitation zone. The substance is prevented from reaching the microphone by supplying a protecting gas to a portion of the waveguide proximate to the microphone. The waveguide is an acoustic resonator in which at least two antinodes of the acoustic signal are present, the resonator being excited in one antinode by the acoustic signal and the microphone being mounted in another antinode such that the waveguide transmits the generated acoustic signal from the substance through the protecting gas to the microphone without any significant weakening of the acoustic signal.

8 Claims, 2 Drawing Sheets

METHOD AND APPARATUS FOR THE TRANSMISION OF AN ACOUSTIC SIGNAL IN A PHOTOACOUSTIC CELL

The invention relates to a method and an apparatus for transmission of an acoustic signal in a photoacoustic or optoacoustic cell which constitutes part of an apparatus for measuring physical or chemical material properties in a medium and/or for analysis of substances/gases or mixtures of these. In the method known as "Photoacoustics" or "Optoacoustics," an acoustic signal produced optically in the medium is measured and the amplitude, frequency or phase of the signal provides information as to the substance composition, density, homogeneity, structure or other properties of the analyzed medium, for instance a smoke gas.

BACKGROUND OF THE INVENTION

From GB-A-2148487 an apparatus for optical analysis of a smoke gas is known. Said apparatus requires, however, an optically clear view, if necessary assisted by mirrors or lenses, of a detection zone through a smoke gas. The zone may be identical to the width of a duct for transporting the smoke gas in that the two nearly identical parts of the apparatus are mounted perpendicularly to the duct and the sensors contained in each part are protected against the harmful effect from the smoke gas by a protective gas fed into each part. The optical signal may vary corresponding to the gas density in the detection zone and is transferred into an electric signal to be read in a meter. The apparatus is only suited for measuring the density of a smoke gas and gives no information as to other essential properties of a gas, such as composition, homogeneity or structure. For that purpose a photoacoustic measurement of the smoke gas has to be made by means of an apparatus allowing the analyzed amount of gas to be introduced into a separate analyzing zone for further examination.

U.S. Pat. No. 3,659,452 discloses a method and an apparatus for photoacoustic spectroscopy of a gas by means of an acoustic resonance cell.

U.S. Pat. No. 4,253,770 discloses an apparatus for optoacoustic analysis by means of the light from a laser resonator and a differential cell assembly.

CH-B-344234 discloses a solely acoustic gas analyzer in which the microphone may be mounted in a side tube to the tube containing the gas sample and be protected against the harmful effects from the analyzed gas by a thin layer of inert gas. A mixing between the analyzed gas and the protecting inert gas has, however, to be considered, and the protection of the microphone is only to be ensured when the relation between the two gases is kept at 100:1. In addition, the mounting of the microphone in a side tube inevitably implies an unwanted weakening of the acoustic signal.

SUMMARY OF THE INVENTION

To optimize the sensitivity of a microphone in a photoacoustic cell for the above analyzing purpose, a mounting of the microphone as close as possible to the source of the acoustic signal is preferred. If this signal is generated at high temperatures in chemical aggressive surroundings or in other surroundings damaging to the microphone, which may often be the case, such mounting may make very great and costly demands on the microphone construction to secure a satisfactory function unless other measures are taken to protect the microphone.

It is therefore the object of the invention to provide a method for isolating a microphone unit in a photoacoustic cell from said damaging surroundings and without the disadvantages associated with the hitherto known mountings of such a unit. It is a further object of the invention to provide an apparatus for carrying out the method.

The foregoing object is attained, according to one aspect of the present invention, by a method for transferring an acoustic signal to a microphone in a photoacoustic cell that is part of an apparatus for photoacoustic analysis of at least one substance and in which apparatus the microphone is protected against the harmful effects from the analyzed substance. The method comprises the steps of placing a microphone for receiving the acoustic signal from an excitation zone, which is located in an environment which is damaging to the microphone, outside of the damaging environment and sonically communicating the microphone with the excitation zone through a waveguide that is at least partly located within the excitation zone. The substance to be analyzed is supplied to the excitation zone, in which zone an acoustic signal is generated by an acoustic frequency modulation of an optical signal directed into the substance in the excitation zone. The substance is prevented from reaching the microphone by supplying a protecting gas to a portion of the of the waveguide proximate to the microphone. The waveguide is an acoustic resonator in which at least two antinodes of the acoustic signal are present in the waveguide, the resonator being excited in one antinode and the microphone being mounted in another antinode such that the waveguide transmits the generated acoustic signal from the substance through the protecting gas to the microphone without any significant weakening of the acoustic signal.

The protecting gas supplied to the waveguide is non-absorbing with respect to the optical signal and thus does not produce sound under illumination by the optical signal, is harmless to the microphone under the physical conditions prevailing in the environment in which it is located in the cell, and is chemically neutral to the substance under the conditions prevailing in the excitation zone.

In some embodiments of the method, the substance to be analyzed is conducted into a portion of the waveguide remote from the microphone, said remote portion of the waveguide constituting at least part of the excitation zone, and the substance and the protecting gas are removed from within the waveguide through an outlet from the waveguide located between the excitation zone and the microphone.

According to another aspect of the invention, there is provided photoacoustic measuring cell comprising a housing having a window adapted to admit into the housing pulsating laser light and a microphone unit a vessel remote from the housing and having a mirror for reflecting the laser light mounted therein, an inlet into the vessel for admitting into the cell a substance to be analyzed which is damaging to the microphone unit, and a waveguide connected between the housing and the vessel. The waveguide has a length such that it constitutes a half wave acoustic resonator with respect to an acoustic signal generated by photoacoustic modulation by the substance of the laser light and allows the microphone to be located outside the damaging range of the substance. A portion of the waveguide proximate to the vessel defines an excitation zone for analyzing the substance. An inlet into the waveguide proximate to the microphone admits protecting gas into the waveguide, and an outlet from the waveguide at the end of the excitation zone nearer the microphone provides for discharging the substance and the protecting gas.

The resonance frequency of the half wave resonator preferably corresponds to the modulating frequency of the laser light or to a multiple of the modulating frequency. The prime tone of the half wave resonator has an antinode at each end of the waveguide. The frequency of resonance of the waveguide differs from the frequency of the photoacoustically generated acoustic signal of the substance being analyzed. The cell may have two or more waveguides symmetrically mounted in relation to the excitation zone.

In a photoacoustic monitoring of, e.g., gas mixtures, an optical signal is used having frequencies, which are absorbed by a component of the mixture, to disclose the presence and the concentration of the component. The optical signal is modulated on an acoustic frequency, and through illumination of the gas mixture the part of the optical signal which is absorbed will be transformed into heat and cause pressure oscillations of the acoustic frequency. The acoustic signal is transformed into an electric signal in a microphone, and the concentration of the absorbing component in the gas mixture is determined through analysis of the electric signal.

In monitoring specific molecules in a smoke gas or in another gas mixture resulting from chemical reactions in a reactor, the acoustic signal should be suitably generated at the temperature of the smoke gas at the sampling location due to the fact that a change in temperature involves the risk of distortion of the sampling results, for instance through condensing of important gas components, disturbance of chemical balances, etc.

Another field of application is monitoring of molecules through absorption lines, the lower energy level being an excited state of the molecules. For such absorption lines the absorption coefficient will rise together with the temperature, causing the sensitivity to increase when heating the gas.

In such monitorings the excitation zone of the applied gas/gases represents an extremely damaging field for a microphone unit and consequently according to the invention the microphone is connected to the excitation zone by means of an acoustic waveguide for transmitting the acoustic signal to the microphone.

DESCRIPTION OF EMBODIMENTS

Figure 1A:
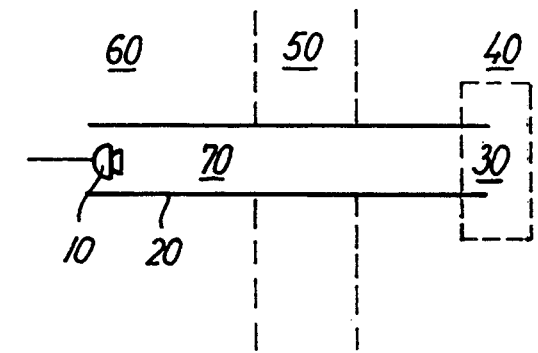
FIGS. 1A, 1B and 1C show diagrammatically three mutually different principles of the method, respectively.

FIG. 1A shows one embodiment of the invention. A microphone 10 is located in an area 60 having a tolerable environment, but the microphone would not endure to be located in the damaging environments 40 containing the acoustic excitation zone 30. A conduit through which the protecting gas 70 can travel serves as an acoustic waveguide which transmits the acoustic signal from the excitation zone 30 via the transition area 50 to the microphone 10.

The protecting gas 70 prevents the microphone from contact with the analyzed substance and is characterized in not exposing the microphone to unacceptable effects under the conditions prevailing in area 60.

The excitation zone 30 may be located fully or partly within the waveguide 20.

Likewise the microphone 10 may be located within the waveguide 20 or immediately outside the latter.

The waveguide 20 may be designed so as to form an acoustic resonator for sound from the modulation frequency or multiples of same, though this may not necessarily be the case.

Figure 1B:
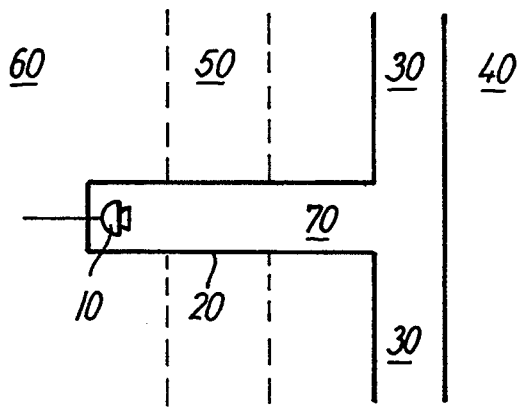
Figure 1C:
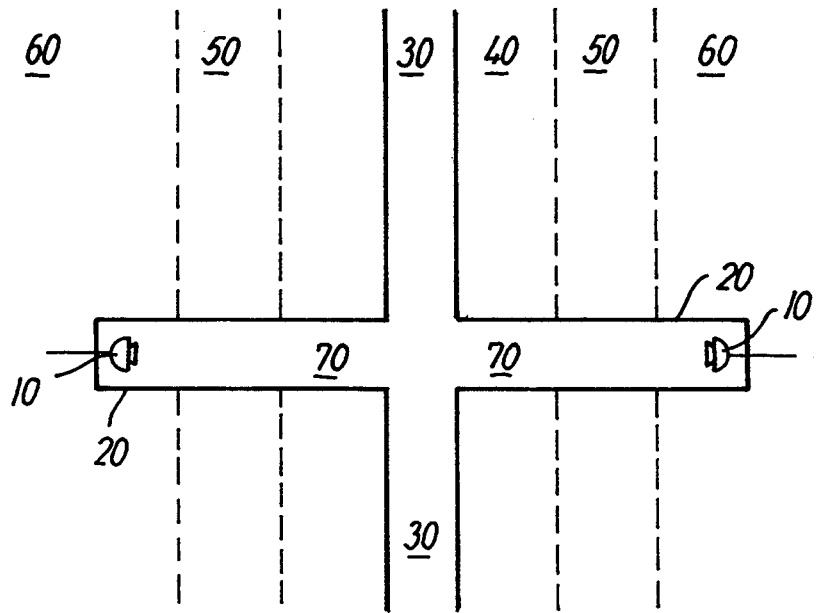

Other basic outlines of the method appear from FIGS. 1B and 1C, FIG. 1B showing an open, resonant excitation zone 30 which does not give the same resonance as in the waveguide 20, whereas FIG. 1C shows an open, resonant excitation zone 30 with two symmetrically placed waveguides 20.

Figure 2:
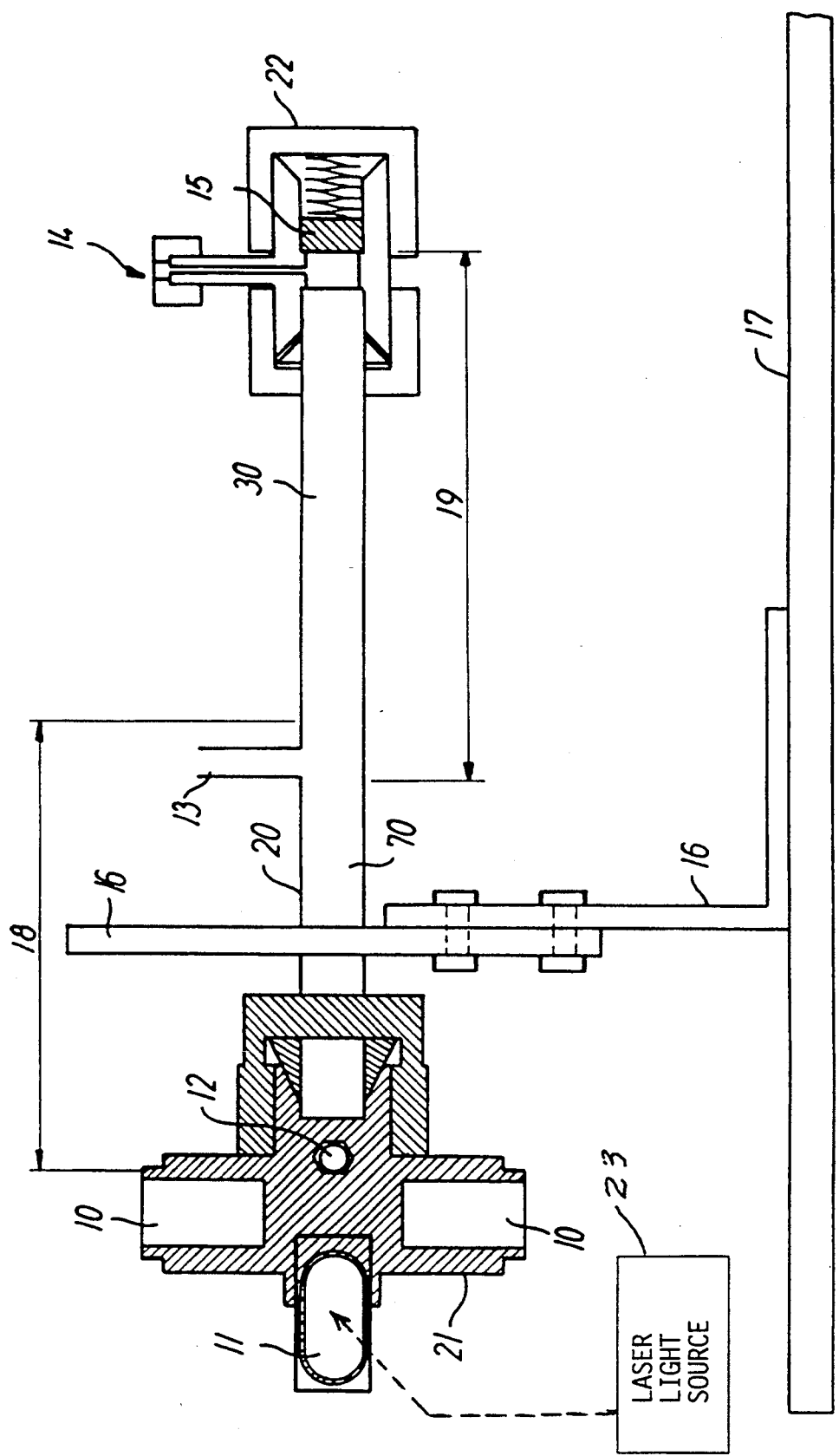
FIG. 2 shows diagrammatically an embodiment of the apparatus.

FIG. 2 shows an embodiment of the apparatus according to the invention, the apparatus being a cell for photoacoustic monitoring at high temperatures. The optical signal which is modulated upon an acoustic frequency is emitted from a waveguide laser 23 (shown diagrammatically) and directed into the cell through a window 11, which together with a microphone unit 10 is mounted in a housing 21 having also one end of an acoustic waveguide 20 located therein. The other end of the waveguide 20 terminates in a vessel 22 having an inlet 14 for introducing a sample of medium, in this case a gas, into the waveguide 20. In direct continuation of the waveguide a mirror mechanism 15 is mounted in the vessel 22 for reflecting in an acute angle the light directed into the waveguide through the window in such matter that the light will leave the cell again through the same window. In the waveguide 20 an outlet 13 is mounted at an appropriate distance from the inlet 14. This distance or space delimited by the inlet 14 and the outlet 13 is denoted as an interaction volume or an excitation zone 19 in which the medium is measured and the acoustic signal generated. To prevent the gas 30 damaging to the microphone unit 10 from reaching the microphone, the housing 21 is provided with an inlet 12 for protecting gas which is conveyed through the housing and the waveguide over a distance or zone 18 in a direction towards the excitation zone and which together with the gas sample is lead out through outlet 13. The cell construction as a whole may be mounted in a support 16 resting upon a base 17. Such protecting gas is selected which is chemically neutral towards the analyzed medium under the prevailing conditions in the excitation zone, and which does not give any absorption and thus no acoustic signal for the utilized light frequencies and which furthermore causes no damaging effects upon the window and the microphone unit. As protecting gas cleaned, atmospheric air may e.g. be used.

The waveguide 20, shown in FIG. 2, forms an acoustic half wave resonator, which amplifies the acoustic field at the resonance frequency. The resonator is closed at both ends, allowing the existence of pressure antinodes (i.e., regions of maximum amplitude of pressure oscillations) at the ends. At resonance, acoustic energy is exchanged between the two antinodes with high efficiency. This allows excitation to take place at one end of the resonator, which may be warm, while the microphone is located at the other end, which may be kept cool. Likewise the shown embodiment of the cell has the advantage of the light being directed through a window located at the cold end of the cell and being reflected by the mirror at the warm end, thereby not exposing the window to extreme effects so as to avoid countermeasures against such effects, as well as to eliminate the need for special sealings at the warm end between the different materials from which the cell is made. Advantageously, the cell may therefore be manufactured as an all-welded unit or as shown in FIG. 2 with steel-steel locking collar sealings.

In corresponding apparatus for the method as outlined in FIGS. 1B and 1C the optical signal (the laser beam) is not necessarily directed into the waveguide(s) 20, but may just as well be directed straight into and along the excitation zone 30 and thus transversely to the waveguide(s).

We claim:

1. A method for transferring an acoustic signal to a microphone in a photoacoustic cell that is part of an apparatus for photoacoustic analysis of at least one gaseous substance and in which apparatus the microphone is protected against the harmful effects from the gaseous substance analyzed, comprising the steps of placing the microphone for receiving the acoustic signal from an excitation zone, which is located in an environment which is damaging to the microphone, outside of the damaging environment, sonically communicating the microphone with the excitation zone through a waveguide that is at least partly located within the excitation zone, supplying the gaseous substance to be analyzed to the excitation zone, in which zone an acoustic signal is generated by an acoustic frequency modulation of an optical signal directed into the gaseous substance in the excitation zone, preventing the gaseous substance from reaching the microphone by supplying a protecting gas to a portion of the waveguide proximate to the microphone, the waveguide being an acoustic resonator in which at least two antinodes of the acoustic signal are present in the waveguide, the resonator being excited in one antinode and the microphone being mounted in another antinode such that the waveguide transmits the generated acoustic signal from the gaseous substance through the protecting gas to the microphone without any significant weakening of the acoustic signal.

2. A method according to claim 1, wherein the protecting gas supplied to the waveguide is non-absorbing with respect to the optical signal and thus does not produce sound under illumination by the optical signal, is harmless to the microphone under the physical conditions prevailing in the environment in which the microphone is located and is chemically neutral to the gaseous substance under the conditions prevailing in the excitation zone.

3. A method according to claim 1, and further comprising the step of conducting the gaseous substance into a portion of the waveguide remote from the microphone, said remote portion of the waveguide constituting at least part of the excitation zone, and removing the gaseous substance and the protecting gas from within the waveguide through an outlet from the waveguide located between the excitation zone and the microphone.

4. A photoacoustic measuring cell comprising a housing (21) having a window (11) adapted to admit into the housing pulsating laser light and a microphone unit (10), a vessel remote from the housing and having a mirror (15) for reflecting the laser light mounted therein, an inlet (14) into the vessel for admitting a gaseous substance to be analyzed which is damaging to the microphone unit (10) and a waveguide (20) connected between the housing (21) and the vessel (22), the waveguide (20) having a length such that it constitutes a half wave acoustic resonator with respect to an acoustic signal generated by photoacoustic modulation by the gaseous substance of the laser light and allows the microphone (10) to be located outside the damaging range of the gaseous substance, a portion of the waveguide (20) proximate to the vessel defining an excitation zone (19) for analyzing the gaseous substance, an inlet (12) into the waveguide proximate to the microphone for admitting protecting gas (70) into the waveguide, and outlet (13) from the waveguide (20) at the end of the excitation zone nearer the microphone for discharging the gaseous substance and the protecting gas.

5. An apparatus according to claim 4, wherein the resonance frequency of the half wave resonator corresponds to the modulating frequency of the laser light or to a multiple of the modulating frequency.

6. An apparatus according to claim 4, wherein the prime tone of the half wave resonator has an antinode at each end of the waveguide.

7. An apparatus according to claim 4, wherein the frequency of resonance of the waveguide differs from the frequency of the photoacoustically generated acoustic signal of the gaseous substance being analyzed.

8. An apparatus according to claim 4, wherein the cell has two or more waveguides symmetrically mounted in relation to the excitation zone (30).

* * * * *

UNITED STATES PATENT AND TRADEMARK OFFICE
CERTIFICATE OF CORRECTION

PATENT NO. : 5,339,674

DATED : August 23, 1994

INVENTOR(S) : Mads Hammerich et al

It is certified that error appears in the above-indentified patent and that said Letters Patent is hereby corrected as shown below:

```
Title Page, Item 73, "Airlog" should read --Airloq--;
    Item 30, 2nd line, "May 3" should read --Mar. 5--.

Col. 6, line 31, "and" should read --and an--.
```

Signed and Sealed this

Sixth Day of December, 1994

Attest:

BRUCE LEHMAN

Attesting Officer        *Commissioner of Patents and Trademarks*